United States Patent
Yotani et al.

(10) Patent No.: US 9,481,881 B2
(45) Date of Patent: Nov. 1, 2016

(54) ELUENT FOR ION-EXCHANGE CHROMATOGRAPHY, AND METHOD OF ANALYZING NUCLEIC ACID CHAINS

(75) Inventors: Takuya Yotani, Ibaraki (JP); Koji Ushizawa, Tokyo (JP)

(73) Assignee: SEKISUI MEDICAL CO., LTD., Tokyo (JP)

(*) Notice: Subject to any disclaimer, the term of this patent is extended or adjusted under 35 U.S.C. 154(b) by 0 days.

(21) Appl. No.: 13/979,241

(22) PCT Filed: Jan. 12, 2012

(86) PCT No.: PCT/JP2012/050426
§ 371 (c)(1),
(2), (4) Date: Aug. 21, 2013

(87) PCT Pub. No.: WO2012/096327
PCT Pub. Date: Jul. 19, 2012

(65) Prior Publication Data
US 2013/0330735 A1    Dec. 12, 2013

(30) Foreign Application Priority Data

Jan. 12, 2011 (JP) .............................. 2011-004216

(51) Int. Cl.
*C07H 21/00* (2006.01)
*C12Q 1/68* (2006.01)
(Continued)

(52) U.S. Cl.
CPC ........... *C12N 15/101* (2013.01); *C12Q 1/6806* (2013.01); *G01N 30/96* (2013.01); *Y10T 436/143333* (2015.01)

(58) Field of Classification Search
CPC .......................... C12N 15/101; C12Q 1/6806
USPC ............ 435/6.1; 422/70; 210/660; 536/25.4
See application file for complete search history.

(56) References Cited

U.S. PATENT DOCUMENTS 4,704,274 A * 11/1987 Sakuma ............... C07K 14/235
424/240.1
(Continued)

FOREIGN PATENT DOCUMENTS

CN     1451762      10/2003
CN     1880480      12/2006
(Continued)

OTHER PUBLICATIONS

Corresponding U.S. Appl. No. 13/979,256, filed Sep. 18, 2013.
(Continued)

*Primary Examiner* — Jezia Riley
(74) *Attorney, Agent, or Firm* — Wenderoth, Lind & Ponack, L.L.P.

(57) ABSTRACT

The present invention provides eluent for ion-exchange chromatography, wherein the eluent allows separation and detection of a target nucleic acid such as a PCR-amplified product, a restriction enzyme fragment of the PCR-amplified product, or a restriction enzyme fragment of a nucleic acid in a short time with high separation performance. The present invention also provides a method of analyzing nucleic acid chains by ion-exchange chromatography using the eluent. The present invention provides an eluent for ion-exchange chromatography comprising a guanidine salt derived from guanidine represented by the following formula (1):

[Chem. 1]

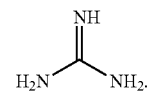

(1)

4 Claims, 3 Drawing Sheets

(51) Int. Cl.
*B01D 15/00* (2006.01)
*C12N 15/10* (2006.01)
*G01N 30/96* (2006.01)
*G01N 30/02* (2006.01)

(56) References Cited

U.S. PATENT DOCUMENTS

| | | |
|---|---|---|
| 5,438,128 A | 8/1995 | Nieuwkerk et al. |
| 2002/0197629 A1 | 12/2002 | Gjerde et al. |
| 2007/0154892 A1 | 7/2007 | Wain-Hobson et al. |
| 2008/0076910 A1 | 3/2008 | Takkellapati et al. |
| 2009/0053719 A1 | 2/2009 | Lo et al. |

FOREIGN PATENT DOCUMENTS

| | | |
|---|---|---|
| CN | 101323852 | 12/2008 |
| CN | 101899437 | 12/2010 |
| CN | 101899511 | 12/2010 |
| DE | 697 29 182 | 1/2005 |
| EP | 2 366 719 | 9/2011 |
| EP | 2692863 | 2/2014 |
| JP | 05-099909 | 4/1993 |
| JP | 2002-187897 | 7/2002 |
| JP | 2004-513625 | 5/2004 |
| JP | 2004-514874 | 5/2004 |
| JP | 2004-180637 | 7/2004 |
| JP | 2005-027518 | 2/2005 |
| JP | 2005-323565 | 11/2005 |
| JP | 2006-075126 | 3/2006 |
| JP | 2009-524412 | 7/2009 |
| JP | 2010-504738 | 2/2010 |
| WO | 97/29825 | 8/1997 |
| WO | 01/27331 | 4/2001 |
| WO | 2007/091125 | 8/2007 |
| WO | 2008/039664 | 4/2008 |
| WO | 2008/039668 | 4/2008 |

OTHER PUBLICATIONS

Corresponding U.S. Appl. No. 14/008,770, filed Dec. 9, 2013.
"Raifusaiensu Notameno Kosoku Ekitai Kuromatogurafi—Kiso To Jikken (High-Performance Liquid Chromatography for Life Science—Basis and Experiment)"; Hirokawa Shoten; 1988; pp. 333-359.
Randall K. Saiki et al.; "Analysis of enzymatically amplified β-globin and HLA-DQα DNA with allele-specific oligonucleotide probes"; Nature; vol. 324; Nov. 1986; pp. 163-166.
International Search Report issued Mar. 19, 2012 in International (PCT) Application No. PCT/JP2012/050426.
D'Anna et al., "Histones H1°a and H1°b Are the Same as CHO Histones H1 (III) and H1 (IV): New Features of H1° Phosphorylation during the Cell Cycle", Biochemistry, vol. 20, Jul. 21, 1981, pp. 4501-4505.
Ghrist et al., "Predicting Bandwidth in the High-Performance Liquid Chromatographic Separation of Large Biomolecules", Journal of Chromatography, vol. 387, 1987, pp. 1-19.
Iny et al., "Isolation of a thermophilic alkaline phosphatase by either hydrophobic or Procion red Sepharose chromatography", Journal of Chromatography, vol. 360, 1986, pp. 437-442.
Gaudet et al., "Allele-Specific PCR in SNP Genotyping", Methods in Molecular Biology, vol. 578, 2009, pp. 415-424.
Tsuchihashi et al., "Progress in high throughput SNP genotyping methods", The Pharmacogenomics Journal, vol. 2, No. 2, 2002, pp. 103-110.
Extended European Search Report issued Nov. 5, 2014 in corresponding European Patent Application No. 12734660.9.
Thayer, J.R. et al. "Control of oligonucleotide retention on a pH-stabilized strong anion exchange column", Analytical Biochemistry, Academic Press Inc., New York. vol. 338, No. 1, pp. 39-47, Mar. 1, 2005.
Gaudet, et al. "Allele specific PCR in SNP genotyping", Single Nucleotide Polymorphisms: Methods and Protocols, Humana Press, USA, pp. 415-423, Jan. 1, 2009.
Huang et al., "A Simple and Rapid Modified New Method for SNP Typing by Fragment Length Discrepant Allele Specific PCR", Journal of Forensic Medicine, vol. 21, No. 1, Feb. 2005, with English language Abstract.
Extended European Search Report issued Dec. 8, 2014 in counterpart European Patent Application No. 12734188.1.
Okimoto, R. et al., "Improved PCR Amplification of Multiple Specific Alleles (PAMSA) Using Internally Mismatched Primers", BioTechniques, vol. 21, pp. 20-26 (Jul. 1996).
Extended European Search Report issued Jan. 23, 2015 in counterpart European Patent Application No. 12765405.01.
Neitzel et al., "Easy, Accurate and Reliable Screening for SNPs by Ion Pair/Reverse Phase HPLC: Simultaneous Detection of Factor V G1691A, Prothrombin G20210A and Methylenetetrahydrofolate Reductase C677T Variants", Clinical Lab, vol. 49, pp. 313-318, 2003.
Seipp et al., "Quadruplex Genotyping of F5, F2, and MTHFR Variants in a Single Closed Tube by High-Resolution Amplicon Melting", Clinical Chemistry, vol. 54, No. 1, pp. 108-115, 2008.
Webster et al., "Analysis of variation in the human β-globin gene cluster using a novel DHPLC technique", Mutation Research, vol. 501, pp. 99-103, 2002.
Yoshio Kato et al., "Separation of DNA restriction fragments by high-performance ion-exchange chromatography on a non-porous ion exchanger", Journal of Chromatography, 1989, vol. 478, No. 1, pp. 264-268.

\* cited by examiner

ELUENT FOR ION-EXCHANGE CHROMATOGRAPHY, AND METHOD OF ANALYZING NUCLEIC ACID CHAINS

TECHNICAL FIELD

The present invention relates to an eluent for ion-exchange chromatography for use in separation and detection of a target nucleic acid such as a PCR-amplified product, a restriction enzyme fragment of the PCR-amplified product, or a restriction enzyme fragment of a nucleic acid. The present invention also relates to a method of analyzing nucleic acid chains by ion-exchange chromatography using the eluent.

BACKGROUND ART

Ion-exchange chromatography is a method of separating a target analyte by utilizing electrostatic interactions between ions in the target analyte and ion-exchange groups in column packing.

Ion-exchange chromatography is particularly excellent in separation of biomacromolecules such as nucleic acids, proteins, and polysaccharides, and thus has been used in the fields of biochemistry, medicine, and the like.

Ion-exchange chromatography is categorized into anion-exchange chromatography and cation-exchange chromatography. Anion-exchange chromatography can separate anionic substances using cationic column packing. In contrast, cation-exchange chromatography can separate cationic substances using anionic column packing.

Examples of cationic functional groups in anion-exchange column packing include weak cationic groups such as a diethylaminoethyl group and strong cationic groups such as a quaternary ammonium group. Anion-exchange column packing containing these cationic functional groups has been commercially available and used in various research fields.

A nucleic acid is a biomacromolecule comprising chains of nucleotides linked by phosphoester bonds, each nucleotide consisting of a base, a sugar, and a phosphoric acid. There are two types of nucleic acids, i.e., deoxyribonucleic acid (DNA) and ribonucleic acid (RNA), depending on the sugar structure.

Ion-exchange chromatographic separation of a target nucleic acid such as a PCR-amplified product, a restriction enzyme fragment of the PCR-amplified product, or a restriction enzyme fragment of a nucleic acid is performed by anion-exchange liquid chromatography that uses phosphate negative charges in the target nucleic acid molecule. This allows separation and detection of each target nucleic acid such as the PCR-amplified product or the nucleic acid fragment by chain length.

Although gel electrophoresis is widely used as a method of separating nucleic acid chains by chain length, it requires complicated operations and long measurement time, thus leaving much room for improvement. Non-Patent Literature 1 discloses a method of separating nucleic acid-related compounds by high-performance liquid chromatography. This method allows separation and detection of nucleic acid chains by chain length in a short time without requiring complicated operations. However, even with this method, it is still difficult to fully separate nucleic acid chains of a similar length. Hence, further improvement in separation performance is required.

CITATION LIST

Non-Patent Literature

Non-Patent Literature 1: "*Raifusaiensu Notameno Kosoku Ekitai Kuromatogurafi—Kiso To Jikken* (High-Performance Liquid Chromatography for Life Science—Basis and Experiment)", Hirokawa Shoten, pp. 333-359.

SUMMARY OF INVENTION

Technical Problem

The present invention aims to provide an eluent for ion-exchange chromatography, wherein the eluent allows separation and detection of a target nucleic acid such as a PCR-amplified product, a restriction enzyme fragment of the PCR-amplified product, or a restriction enzyme fragment of a nucleic acid in a short time and with high separation performance. The present invention also aims to provide a method of analyzing nucleic acid chains by ion-exchange chromatography using the eluent.

Solution to Problem

The present invention is an eluent for ion-exchange chromatography comprising a guanidine salt derived from guanidine represented by formula (1) below. The present invention is described in detail below.

[Chem. 1]

The present inventors found that addition of a guanidine salt to an eluent for ion-exchange chromatography results in improved separation performance for samples of different nucleic acid chain lengths, and the present invention was accomplished based on such finding.

An eluent for ion-exchange chromatography of the present invention comprises a guanidine salt derived from guanidine represented by the above formula (1).

Examples of the guanidine salt include guanidine hydrochloride, guanidine sulfate, guanidine nitrate, guanidine carbonate, guanidine phosphate, guanidine thiocyanate, guanidine sulfamate, aminoguanidine hydrochloride, and aminoguanidine bicarbonate. In particular, guanidine hydrochloride and guanidine sulfate are suitably used.

The concentration of a guanidine salt in the eluent when analyzed may be properly adjusted in accordance with a substance to be detected; however, it is preferably 2,000 mmol/L or less.

Specifically, a method can be mentioned which involves performing gradient elution in the guanidine salt concentration range of 0 to 2,000 mmol/L. Thus, it is not necessary that the concentration of the guanidine salt in starting analysis is 0 mmol/L, and it is also not necessary that the concentration of the guanidine salt in terminating analysis is 2,000 mmol/L.

The method of gradient elution may be a low-pressure gradient method or a high-pressure gradient method; however, a method is preferable which involves carrying out elution while performing precise concentration adjustment by the high-pressure gradient method.

The guanidine salt may be added alone or in combination with other salts to the eluent. Examples of the salts that can be used in combination with the guanidine salt include salts formed from alkali metals and halides such as sodium chloride, potassium chloride, sodium bromide, and potassium bromide; salts formed from alkaline earth metals and halides such as calcium chloride, calcium bromide, magnesium chloride, and magnesium bromide; and inorganic acid salts such as sodium perchlorate, potassium perchlorate, sodium sulfate, potassium sulfate, ammonium sulfate, sodium nitrate, and potassium nitrate. Organic acid salts such as sodium acetate, potassium acetate, sodium succinate, and potassium succinate may also be used.

Any known buffer or organic solvent can be used as a buffer in the eluent for ion-exchange chromatography of the present invention. Specific examples include a Tris-hydrochloric acid buffer; a TE buffer comprising Tris and EDTA; a TAE buffer comprising Tris, acetic acid, and EDTA; and a TBA buffer comprising Tris, boric acid, and EDTA.

The pH of the eluent is not particularly limited, and may be in the range allowing the separation of nucleic acid chains by anionic exchange.

A method of analyzing nucleic acid chains using the eluent for ion-exchange chromatography of the present invention is another aspect of the present invention.

Any anion-exchange column packed with cationic packing may be used as a column for the method of analyzing nucleic acid chains of the present invention. Examples include commercially available anion-exchange columns, and anion-exchange columns with packing containing strong cationic groups and weak anionic groups on the surface of base fine particles.

The method of analyzing nucleic acid chains of the present invention is applicable to the following target nucleic acids (objects to be detected): PCR-amplified products, restriction enzyme fragments of the PCR-amplified products, and restriction enzyme fragments of nucleic acids. Examples include virus-derived nucleic acids and human-derived nucleic acids that may be genetically polymorphic, i.e., virus-derived nucleic acids (DNA and RNA) for identifying the presence and type of virus, and human-derived DNA for identifying gene polymorphism (single nucleotide polymorphism).

The above DNA or RNA is extracted and purified by a known method, and amplified, if necessary, by polymerase chain reaction (PCR) or the like. Then, the amplified product is provided in ion-exchange chromatography that uses the eluent for ion-exchange chromatography of the present invention.

When a virus is an RNA virus or the like, an extracted and purified RNA may be subjected to reverse transcription polymerase chain reaction (RT-PCR) to thereby obtain a PCR-amplified product.

Further, when the method of analyzing nucleic acid chains of the present invention is used to identify gene polymorphism, a technique known as a PCR-restriction fragment length polymorphism (RFLP) method can be used. According to the RFLP method, when there is a restriction enzyme that recognizes a mutation region in a PCR-amplified product, primers are placed in a common sequence site, and the region between the primers is amplified such that the PCR-amplified product has polymorphism. Then, the obtained PCR-amplified products are cut with the restriction enzyme, and the presence or absence of polymorphism is determined based on the lengths of these fragments. The number and size of produced fragments vary depending on whether the PCR-amplified products were cut with the restriction enzyme. Thus, these differences reflect whether cutting was performed and what base is located at a target position.

The region to be amplified by primers is set to such a size that two fragments to be produced in the event of restriction enzyme cutting can be clearly detected by ion-exchange chromatography that uses the eluent for ion-exchange chromatography of the present invention, specifically in a manner that a smaller fragment preferably will have a length of 1 bp or more and more preferably 20 bp or more. The region is also set such that two fragments to be produced will be different in size preferably by 1 bp or more and more preferably by 20 bp or more in order to ensure clear detection by the method of analyzing nucleic acid chains of the present invention. Although the upper limit of the size of the amplified region is not particularly defined, PCR requires more time and cost if the region is too large, and this offers no advantage. Thus, a length of 1000 bp or less is preferred. The base length of the primers is not particularly limited as long as each primer can perform its function. For example, the base length of the primers is 15 to 30 bp, and preferably 20 to 25 bp.

Amplification by the PCR may be carried out in a single round. Alternatively, in order to enhance the sensitivity, a wider region may be amplified by a first-round PCR, and a region contained in the amplified product obtained in the first-round PCR may be further amplified by a second-round PCR, using the PCR-amplified product as a template (nested PCR). In this case, both primers used in the second-round PCR may be different from those used in the first-round PCR; or, only one of the primers may be different and the other primer may be one of those used in the first-round PCR (hemi-nested PCR).

The PCR is known per se, and kits for separation and detection by PCR are commercially available. Thus, PCR can be easily performed. In regard to design of primers and conditions for DNA amplification for PCR, reference can be made to *Molecular Cloning: A Laboratory Manual* (3rd ed.), Volume 2, Chapter 8, pp. 8.1 to 8.126, Cold Spring Harbor Laboratory Press, Cold Spring Harbor, 2001.

Advantageous Effects of Invention

The present invention provides an eluent for ion-exchange chromatography, wherein the eluent allows separation and detection of a target nucleic acid such as a PCR-amplified product, a restriction enzyme fragment of the PCR-amplified product, or a restriction enzyme fragment of a nucleic acid in a short time and with high separation performance. The present invention also provides a method of analyzing nucleic acid chains, wherein the method allows precise analysis of a target nucleic acid in a short time by ion-exchange chromatography using the eluent for ion-exchange chromatography.

DESCRIPTION OF EMBODIMENTS

Figure 1:
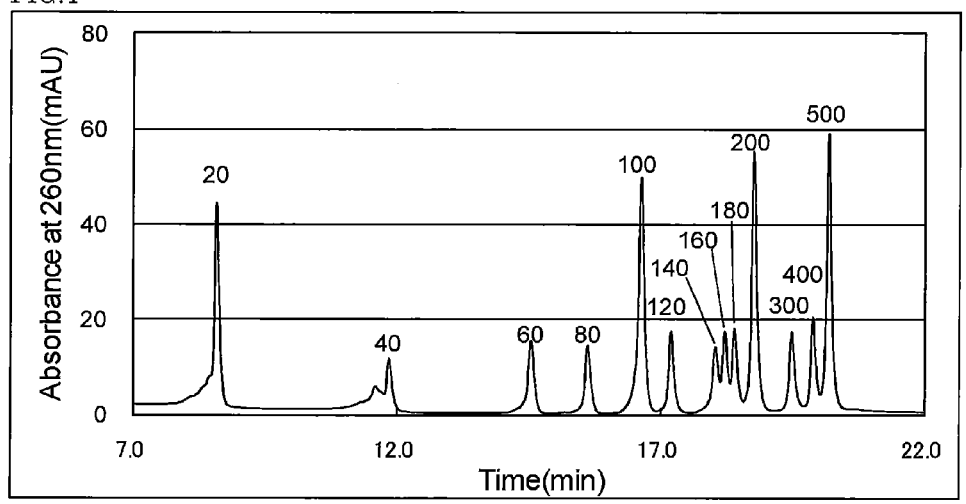
FIG. 1 is a chromatogram obtained using an eluent for ion-exchange chromatography of Example 1 and column 1.

The present invention is described in further detail below with reference to the examples; however, the present invention is not limited to these examples.

Examples 1 and 2 and Comparative Examples 1 to 3

Salts shown in Table 1 were added to 25 mmol/L of Tris-hydrochloric acid buffer to a concentration of 1000 mmol/L to prepare eluents for ion-exchange chromatography of Examples 1 and 2 and Comparative Examples 1 to 3. All of the prepared eluents had a pH of 7.5.

Evaluation

Confirmation of Separation Performance

By the following manner, the eluents for ion-exchange chromatography prepared in the examples and the comparative examples were used to separate and detect target nucleic acids so as to compare the separation performance of these eluents.

Preparation of Anion-Exchange Columns

Anion-Exchange Column 1

As a commercially available column, the following column (anion-exchange column 1) was provided.
Product name: TSK-gel DNA-STAT (manufactured by Tosoh Corporation)
Column size: 4.6 mm (inside diameter)×100 mm (length)
Ion-exchange group: quaternary ammonium group Anion-Exchange Column 2

In a reaction vessel with a stirrer, to a 3 wt % aqueous solution of polyvinyl alcohol (manufactured by The Nippon Synthetic Chemical Industry Co., Ltd.) was added a mixture containing 300 g of tetraethylene glycol dimethacrylate (manufactured by Shin-Nakamura Chemical Co., Ltd.), 100 g of triethylene glycol dimethacrylate (manufactured by Shin-Nakamura Chemical Co., Ltd.), and 1.0 g of benzoyl peroxide (manufactured by Kishida Chemical Co., Ltd.).

The resulting mixture was heated under stirring and polymerized at 80° C. in a nitrogen atmosphere for one hour. Next, as a monomer having a strong cationic ion-exchange group (quaternary ammonium group), 100 g of ethyl methacrylate trimethylammonium chloride (manufactured by Wako Pure Chemical Industries) was dissolved in ion-exchange water, and the obtained solution was further added to the above reaction vessel. Then, the resulting mixture was polymerized under stirring at 80° C. in a nitrogen atmosphere for two hours, thus obtaining a polymer composition. The obtained polymer composition was washed with water and acetone. Thereby, hydrophilic-coated polymer particles having ion-exchange groups on the base particle surface were obtained. The obtained coated polymer particles had an average particle size of 10 μm as measured using a particle size analyzer (Accusizer 780 manufactured by Particle Sizing Systems).

Then, 10 g of the obtained coated polymer particles were immersed in 300 mL of ozone water having a dissolved ozone concentration of 100 ppm, and the mixture was stirred for 30 minutes. After stirring, the mixture was centrifuged using a centrifuge (Himac CR20G manufactured by Hitachi, Ltd.), and the supernatant was removed. This operation was repeated twice, and the coated polymer particles were thereby treated with ozone water. Thus, packing for ion-exchange chromatography having a quaternary ammonium group and a carboxy group was obtained.

The ozone water was prepared using an ozone water production system (manufactured by Sekisui Chemical Co., Ltd.) including an ozone dissolution module that comprises a pillar-shaped outer casing of 15 cm (inside diameter)×20 cm (length), and 400 ozone permeable membranes inside the outer casing, wherein each ozone permeable membrane is formed of perfluoroalkoxy resin and has a hollow tubular shape of 0.5 mm (inside diameter)×0.04 mm (thickness)× 350 cm (length).

The following column (anion-exchange column 2) was prepared using the obtained packing for ion-exchange chromatography.
Column size: 4.6 mm (inside diameter)×20 mm
Ion-exchange group: quaternary ammonium group Using the prepared anion-exchange column, the target nucleic acid was separated and detected under the following conditions.
System: LC-20A series (manufactured by Shimadzu Corporation)
Eluent: solution A (25 mmol/L of Tris-hydrochloric acid buffer (pH 7.5)), and solution B (each eluent prepared in the examples and the comparative examples)
Elution method: the mixing fraction of each solution B was linearly increased over a period from 0 to 20 minutes according to gradient conditions shown in Table 1.
Analyte: 20-bp DNA Ladder marker (manufactured by Takara Bio Inc., containing fragments of 20, 40, 60, 80, 100, 120, 140, 160, 180, 200, 300, 400, and 500 bp)
Flow rate: 0.5 mL/min (anion-exchange column 1), 1.0 mL/min (anion-exchange column 2)
Detection wavelength: 260 nm
Amount of injected sample: 10 μL

TABLE 1

| | | Salt concentration (mmol/L) | Gradient Conditions | |
|---|---|---|---|---|
| | Salts | | Anion-exchange column 1 | Anion-exchange column 2 |
| Examaple 1 | Guanidine hydrochloride | 1000 | 0 minutes (B60%) → 20 minutes (B100%) | 0 minutes (B0%) → 20 minutes (B100%) |

TABLE 1-continued

| | Salts | Salt concentration (mmol/L) | Gradient Conditions | |
|---|---|---|---|---|
| | | | Anion-exchange column 1 | Anion-exchange column 2 |
| Examaple 2 | Guanidine sulfate | 1000 | — | 0 minutes (B0%) → 20 minutes (B100%) |
| Comparataive Examaple 1 | Sodium chloride | 1000 | 0 minutes (B70%) → 20 minutes (B100%) | 0 minutes (B0%) → 20 minutes (B100%) |
| Comparataive Examaple 2 | Sodium perchlorate | 1000 | 0 minutes (B35%) → 20 minutes (B40%) | 0 minutes (B0%) → 20 minutes (B20%) |
| Comparataive Examaple 3 | Ammonium sulfate | 1000 | — | 0 minutes (B0%) → 20 minutes (B100%) |

Figure 2:
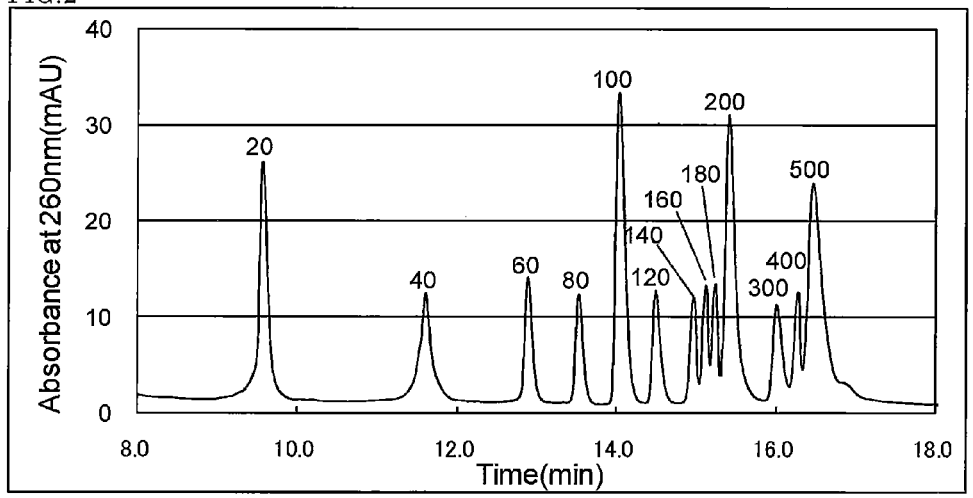
FIG. 2 is a chromatogram obtained using an eluent for ion-exchange chromatography of Example 1 and column 2.
Figure 3:
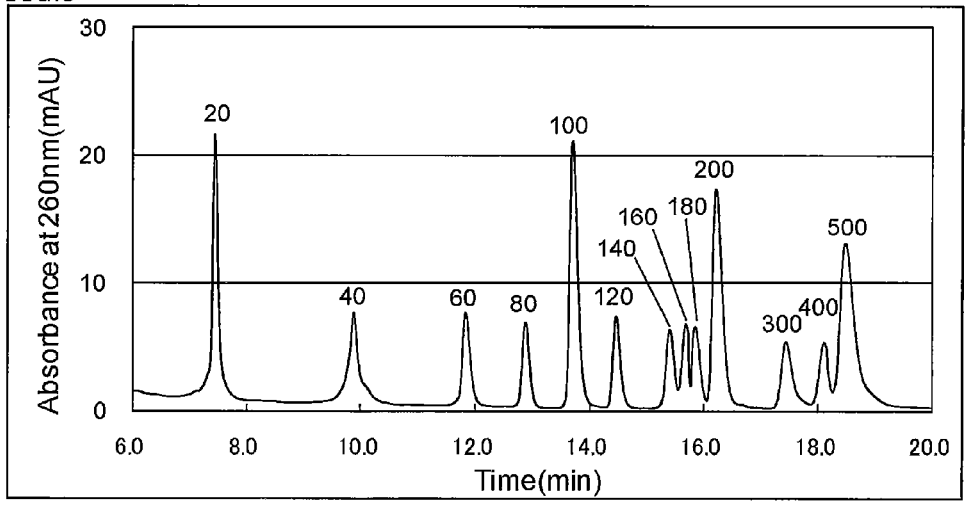
FIG. 3 is a chromatogram obtained using an eluent for ion-exchange chromatography of Example 2 and column 2.
Figure 4:
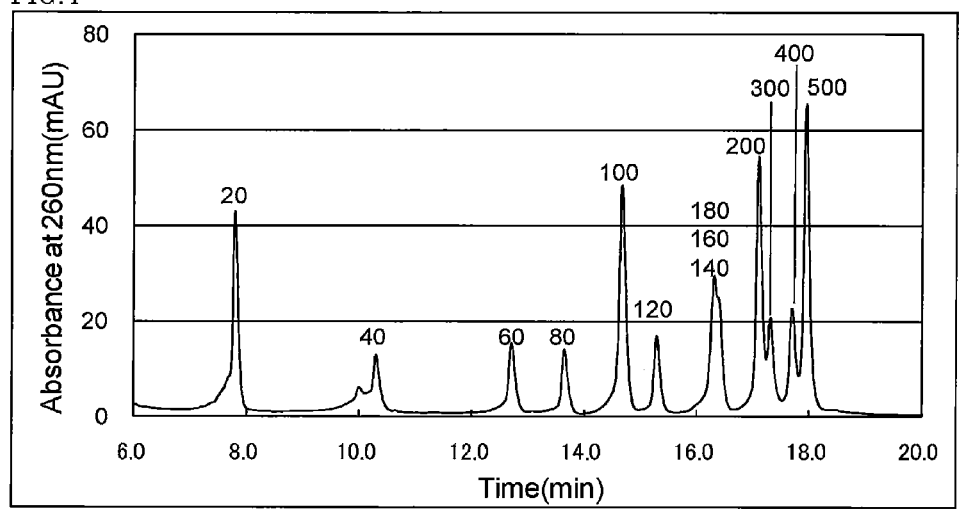
FIG. 4 is a chromatogram obtained using an eluent for ion-exchange chromatography of Comparative Example 1 and column 1.
Figure 5:
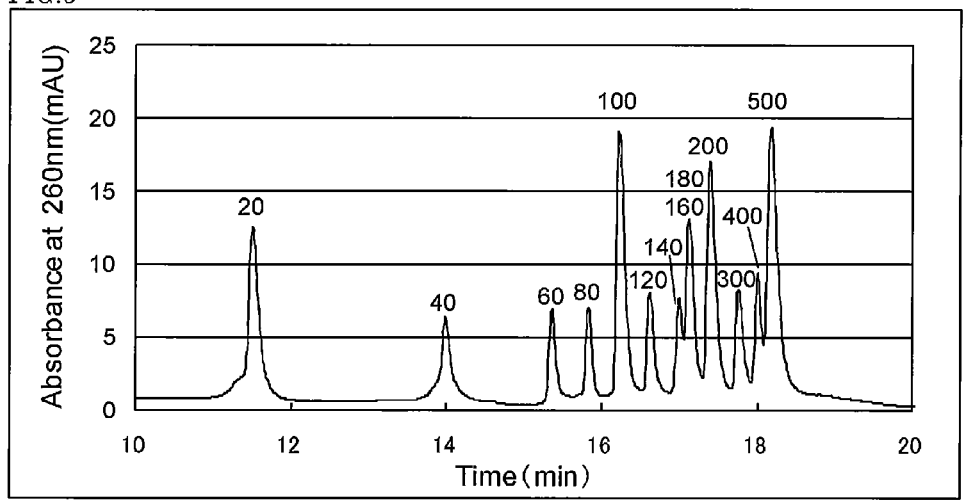
FIG. 5 is a chromatogram obtained using an eluent for ion-exchange chromatography of Comparative Example 1 and column 2.
Figure 6:
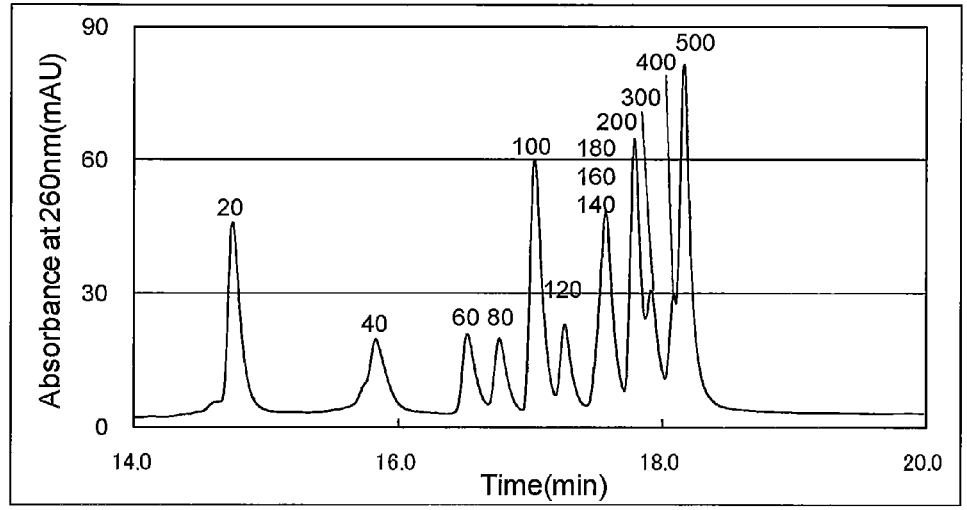
FIG. 6 is a chromatogram obtained using an eluent for ion-exchange chromatography of Comparative Example 2 and column 1.
Figure 7:
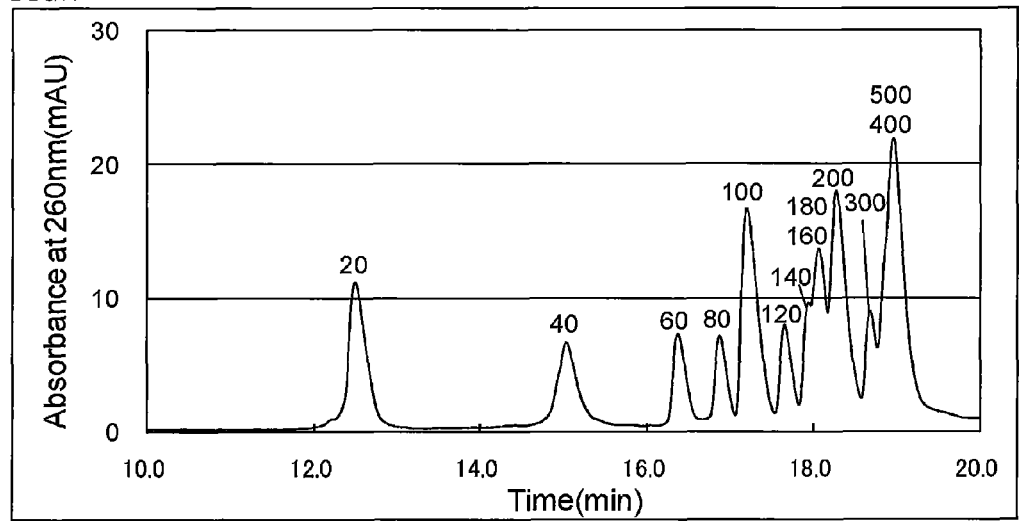
FIG. 7 is a chromatogram obtained using an eluent for ion-exchange chromatography of Comparative Example 2 and column 2.
Figure 8:
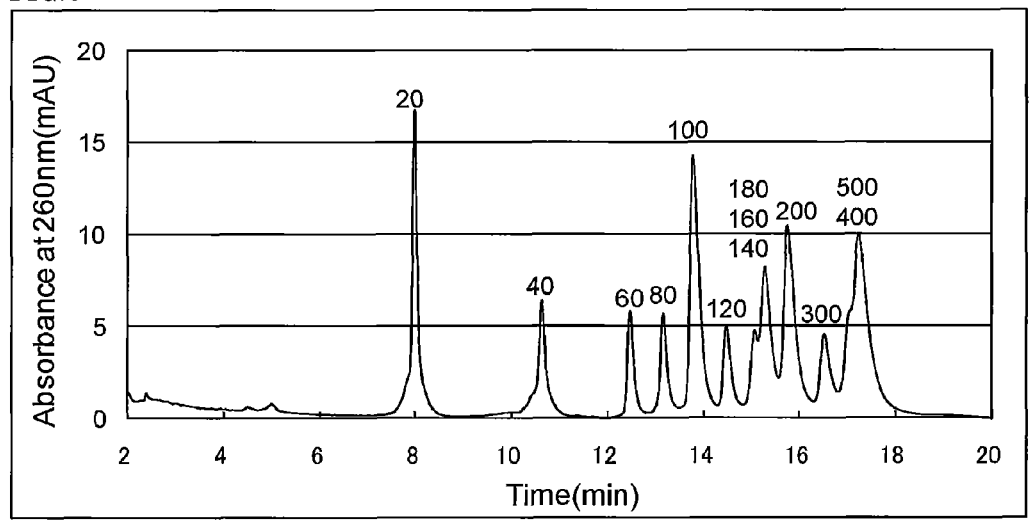
FIG. 8 is a chromatogram obtained using an eluent for ion-exchange chromatography of Comparative Example 3 and column 2.

FIG. 1 shows a chromatogram obtained using an eluent for ion-exchange chromatography of Example 1 and column 1; FIG. 2 shows a chromatogram obtained using an eluent for ion-exchange chromatography of Example 1 and column 2; FIG. 3 shows a chromatogram obtained using an eluent for ion-exchange chromatography of Example 2 and column 2; FIG. 4 shows a chromatogram obtained using an eluent for ion-exchange chromatography of Comparative Example 1 and column 1; FIG. 5 shows a chromatogram obtained using an eluent for ion-exchange chromatography of Comparative Example 1 and column 2; FIG. 6 shows a chromatogram obtained using an eluent for ion-exchange chromatography of Comparative Example 2 and column 1; FIG. 7 shows a chromatogram obtained using an eluent for ion-exchange chromatography of Comparative Example 2 and column 2; and FIG. 8 shows a chromatogram obtained using an eluent for ion-exchange chromatography of Comparative Example 3 and column 2. Numbers in the graphs in FIGS. 1 to 8 indicate base lengths (bp) of fragments.

FIGS. 1 to 8 show that the eluents for ion-exchange chromatography of the examples successfully separated all the fragments contained in the analyte. Clearly, separation performance was effectively improved regardless of the type of columns. On the other hand, although there was some variation depending on the type of columns and the type of salts added, the eluents for ion-exchange chromatography of the comparative examples resulted in insufficient separation of fragments of 140 bp or longer.

INDUSTRIAL APPLICABILITY

The present invention provides an eluent for ion-exchange chromatography, wherein the eluent allows separation and detection of a target nucleic acid such as a PCR-amplified product, a restriction enzyme fragment of the PCR-amplified product, or a restriction enzyme fragment of a nucleic acid in a short time with high separation performance. The present invention also provides a method of analyzing nucleic acid chains in a short time and with high precision by ion-exchange chromatography using the eluent for ion-exchange chromatography.

The invention claimed is:

1. A method of separating nucleic acid chains by chain length, which comprises:
    a step of providing an ion-exchange column with nucleic acid chains bound thereto; and
    a step of eluting the ion-exchange column with an ion-exchange chromatography eluent comprising a guanidine hydrochloride or a guanidine sulfate and thereby separating the nucleic acid chains having different chain lengths.

2. The method according to claim 1, wherein a flow rate of the eluent in the step of eluting is 0.5 mL/min or more to 1.0 mL/min or less.

3. The method according to claim 1, wherein a concentration of the guanidine hydrochloride or the guanidine sulfate in the eluent is 1000 mmol/L or more to 2000 mmol/L or less.

4. The method according to claim 1, wherein a pH of the eluent is approximately 7.5.

* * * * *